US011723907B2

(12) United States Patent
Maciejewski et al.

(10) Patent No.: US 11,723,907 B2
(45) Date of Patent: Aug. 15, 2023

(54) ANTI-AGING COMPOUNDS (71) Applicant: THE CLEVELAND CLINIC FOUNDATION, Cleveland, OH (US)

(72) Inventors: Jaroslaw Maciejewski, Beachwood, OH (US); Sergei Vatolin, Bay Village, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 594 days.

(21) Appl. No.: 16/488,096

(22) PCT Filed: Feb. 23, 2018

(86) PCT No.: PCT/US2018/019454
§ 371 (c)(1),
(2) Date: Aug. 22, 2019

(87) PCT Pub. No.: WO2018/156917
PCT Pub. Date: Aug. 30, 2018

(65) Prior Publication Data
US 2020/0061064 A1 Feb. 27, 2020

Related U.S. Application Data (60) Provisional application No. 62/462,558, filed on Feb. 23, 2017.

(51) Int. Cl.
A61K 31/513 (2006.01)
A61K 31/136 (2006.01)

(52) U.S. Cl.
CPC .......... A61K 31/513 (2013.01); A61K 31/136 (2013.01)

(58) Field of Classification Search
None
See application file for complete search history.

(56) References Cited

U.S. PATENT DOCUMENTS 5,478,821 A 12/1995 Bloy et al.
7,074,925 B1 * 7/2006 Ashkinazi

FOREIGN PATENT DOCUMENTS

WO 1994/27605 A1 12/1994
WO 1995/00112 A1 1/1995

OTHER PUBLICATIONS

Bigarella, Carolina L., Raymond Liang, and Saghi Ghaffari. "Stem cells and the impact of ROS signaling." Development 141.22 (2014): 4206-4218.
Bonkowski, Michael S., and David A. Sinclair. "Slowing ageing by design: the rise of NAD+ and sirtuin-activating compounds." Nature reviews Molecular cell biology 17.11 (2016): 679-690.
Lee, Byung-Hoon, et al. "Enhancement of proteasome activity by a small-molecule inhibitor of USP14—Supplementary Information." Nature 467.7312 (2010): 179-184.
Cai, Sui Xiong, et al. "Synthesis and structure—activity relationships of 1, 2, 3, 4-tetrahydroquinoline-2, 3, 4-trione 3-oximes: novel and highly potent antagonists for NMDA receptor glycine site." Journal of medicinal chemistry 39.17 (1996): 3248-3255.
Oleevskaya, M.S., "Synthesis of 6-bromo-1,2naphthoquinone", Database Caplus, Chemical Abstracts Service, Columbus, Ohio, US, Jan. 1, 1979.
Mohamded, E.A., "Some more new quinolones of expected biological activity", Database Caplus, Chemical Abstracts Service, Columbus, Ohio, US, Jan. 1, 1995.
Dillin, Andrew, Daniel E. Gottschling, and Thomas Nyström. "The good and the bad of being connected: the integrons of aging." Current opinion in cell biology 26 (2014): 107-112.
Elslager, Edward F., Leslie M. Werbel, and Donald F. Worth. "Synthetic schistosomicides. XIV. 1,4-naphthoquinone mono (O-acyloximes), 4-amino-1, 2-naphthoquinones, 2-amino-3-chloro-1, 4-naphthoquinones, and other naphthoquinones." Journal of medicinal chemistry 13.1 (1970): 104-109.
Fang, Evandro Fei, et al. "NAD+ replenishment improves lifespan and healthspan in ataxia telangiectasia models via mitophagy and DNA repair." Cell metabolism 24.4 (2016): 566-581.
Fang, Evandro F., et al. "NAD+ in aging: molecular mechanisms and translational implications." Trends in molecular medicine 23.10 (2017): 899-916.
Fieser, Mary. Fieser and Fieser's Reagents for Organic Synthesis, vol. 14. Wiley, 1989, Publisher's description of publication.
Giorgio, Marco, et al. "Hydrogen peroxide: a metabolic by-product or a common mediator of ageing signals?." Nature reviews Molecular cell biology 8.9 (2007): 722-728.
Greenberg, Edward F., and Sergei Vatolin. "Symbiotic Origin of Aging." Rejuvenation research 21.3 (2018) 225-231.
Guidi, Novella, and Hartmut Geiger. "Rejuvenation of aged hematopoietic stem cells." Seminars in hematology. vol. 54. No 1. WB Saunders, 2017, pp. 51-55.
Ingram, Donald K., et al. "Development of calorie restriction mimetics as a prolongevity strategy." Annals of the New York Academy of Sciences 1019.1 (2004): 412-423.
Jezek, Jan, Katrina F. Cooper, and Randy Strich. "Reactive oxygen species and mitochondrial dynamics: the yin and yang of mitochondrial dysfunction and cancer progression " Antioxidants 7.1 (2018): 13.
Jimenez-Hidalgo, Maria, et al. "NQR1 controls lifespan by regulating the promotion of respiratory metabolism in yeast." Aging cell 8.2 (2009): 140-151.
Lee, Byung-Hoon, et al. "Enhancement of proteasome activity by a small-molecule inhibitor of USP14." Nature 467.7312 (2010): 179-184.

(Continued)

Primary Examiner — Savitha M Rao
Assistant Examiner — Gregg Polansky
(74) Attorney, Agent, or Firm — Tarolli, Sundheim, Covell & Tummino L.L.P.

(57) ABSTRACT

Anti-aging compounds identified using the lead compounds violuric acid and 1-naphthoquinone-2-monoxime are described. The compounds are redox catalysts that appear to improve the function of hematopoietic stem cells. The compounds can be used to decrease the rate of aging in a subject, or to treat or decrease the risk of developing an age-related disease or disorder.

2 Claims, 8 Drawing Sheets (56) References Cited

OTHER PUBLICATIONS

Leskovac, Vladimir, et al. "Reduction of aryl-nitroso compounds by pyridine and flavin coenzymes." The International journal of biochemistry 21.8 (1989): 825-834.

Maher, Pamela. "The effects of stress and aging on glutathione metabolism." Ageing research reviews 4.2 (2005): 288-314.

Neff, Frauke, et al. "Rapamycin extends murine lifespan but has limited effects on aging." The Journal of clinical investigation 123.8 (2013): 3272-3291.

Orr, William C., Svetlana N. Radyuk, and Rajindar S. Sohal. "Involvement of redox state in the aging of Drosophila melanogaster." Antioxidants & redox signaling 19.8 (2013): 788-803.

PCT International Search Report and Written Opinion for corresponding International Application Serial No. PCT/US2018/019454, dated Jan. 3, 2018, pp. 1-21.

Podhorecka, Monika, Blanca Ibanez, and Anna Dmoszynska. "Metformin-its potential anti-cancer and anti-aging effects." Advances in Hygiene & Experimental Medicine/Postepy Higieny i Medycyny Doswiadczalnej 71 (2017), pp. 170-175.

Ponnappan, Subramaniam, et al. "Compensatory increase in USP14 activity accompanies impaired proteasomal proteolysis during aging." Mechanisms of ageing and development 134. 1-2 (2013): 53-59.

Shukla, S., et al. "Synthesis, characterization and antiproliferative activity of 1, 2-naphthoquinone and its derivatives " Applied biochemistry and biotechnology 167.5 (2012): 1430-1445.

Yoo, Eun-Hyung, and Soo-Youn Lee. "Glucose biosensors: an overview of use in clinical practice." Sensors 10.5 (2010): 4558-4576.

* cited by examiner

ANTI-AGING COMPOUNDS

CROSS-REFERENCE TO RELATED APPLICATIONS

This application is a national phase application of and claims priority to PCT International Patent Application PCT/US2018/019454, filed Feb. 23, 2018, which claims priority to U.S. Provisional Application No. 62/462,558, filed Feb. 23, 2017. Each of the above-identified applications is hereby incorporated by reference in its entirety.

BACKGROUND

Currently, there is no effective pharmacological treatment of aging in humans or any other mammalian species. However, positive experimental data have been obtained on mice after treatment with rapamycin or metformin. Neff et al., J Clin Invest., 123(8), 3272-91 (2013). Rapamycin is an immunosuppressive macrolide that is used to prevent organ rejection after transplantation. While is has shown the ability to increase lifespan in the mouse model, it has a complicated chemical structure, making it difficult to optimize through structure-activity studies, has poor water solubility, and a number of undesirable side-effects. Metformin is more promising, and is currently undergoing clinical trials for protective effects against several age-related diseases and the ability to extend human lifespan. Podhorecka et al., Postepy Hig Med Dosw (Online), 71(0):170-175 (2017). Unfortunately, the mechanism of action of metformin resulting in these effects is poorly understood, which again complicates the development of additional compound using structure-activity studies. Research has also been carried out to evaluate the effect of energy restriction mimetic agents on lifespan. See Ingram et al., Ann N Y Acad Sci., 1019 p. 412-23 (2004).

Tissue homeostasis is driven by adult stem cells whose fate is dependent on the proper balance between self-renewal and differentiation throughout life. More evidence is accumulating that redox balance in both embryonic and adult stem cells is under control of reactive oxygen species (ROS)(Bigarella et al., Development 141, 4206-4218 (2014)). However, it was not clear whether oxidative stress was the result of a genetic program or the by-product of physiological processes. Recent findings demonstrate that a fraction of mitochondrial $H_2O_2$, produced by a specialized enzyme as a signalling molecule in the pathway of apoptosis, induces intracellular oxidative stress and accelerates aging. Giorgio et al., Nat Rev Mol Cell Biol., 8, 722-728, (2007). The metabolism of aging cells and organisms gradually shifts toward glycolysis and less effective mitochondrial functions. Greenberg E., Vatolin, S., Rejuvenation research, 1973 (2017). It's well established that stem cells highly depend on glycolysis-based production of energy and corresponding amplification of anaplerotic metabolic pathways, while differentiated cells mostly derive the energy from respiratory activity of mitochondria. Aging and various pathophysiologic processes are associated with disturbed redox balance which is controlled by oxidized/reduced glutathione ratio (2GSH/GssG). Maher, P., Aging research reviews 4, 288-314, (2005). Currently, drugs targeting stem cell redox balance do not exist, but they could constitute a new class of therapeutics useful for slowing aging.

SUMMARY OF THE INVENTION

Based on the mechanism of action of lead compounds violuric acid and 1-naphthoquinone-2-monoxime, the inventors hypothesized that both of these drugs and potentially their analogs may considerably improve the maintenance of redox balance during the aging process or in disease by providing an extra source of reduced glutathione or modulating signaling by highly reactive molecules like peroxide.

The present invention represents a development of a new class of redox based catalysts directly acting on hematopoietic stem cells (HSC) and which thereby would have a wide application. Examples of indications include retardation of age-related changes of hematopoiesis with a potential of decreasing the rate of cytopenias, improved recovery of blood cell production following iatrogenic insults including chemotherapy and hematopoietic stem cell transplant (HSCT) in therapy of HSC failure in aplastic anemia (AA) or myelodysplastic syndrome (MDS). The ability to increase stem cell function constitutes an opportunity for improvement of HSC function and numbers in patients with refractory disease, whose prognosis is poor including high morbidity and mortality. However, such agents could also be used to speed up recovery following standard treatment, successful immunosuppression therapy (IST), or to improve the quality of responses. To date most of the recovered patients retain some level of impairment of hematopoiesis. Use of anabolic steroids and early acting growth factors indicate that it is possible to stimulate hematopoietic recovery on the level of HSC.

While performing a multidrug screen for the agents that could simultaneously decrease senescence and overcome proliferative block in pre-senescent mesenchymal cells, the inventors identified two promising lead compounds violuric acid (VA) and 1-naphthoquinone-2-monoxime (N2N1). Both drugs demonstrated remarkable properties: expansion of normal fibroblasts and mesenchymal cells for ~25 doublings correspondingly above their regular replicative life span. Both compounds also increased the replicative life span of progeroid fibroblasts isolated from Bloom syndrome patient. In term of hematopoietic stem cells (HSC) these agents prolonged the availability of HSC in methylcellulose (replicative/serial re-plating) experiments, long-term culture initiating cell assays (LTC-IC) and increased the performance of HSC in a competitive repopulation assay, the CD45.1/2 model. Furthermore, the inventors observed colonies formation in methylcellulose colony assay, after application of these drugs to the mononucleocyte fraction of bone marrow isolated from the patients diagnosed with severe AA. Additional studies indicated that these agents do not promote growth of leukemic cell. These compounds belong to a family of redox catalysts with unique chemical structure that shares a combined electrophile-nucleophile potential, a feature that renders these molecules effective anti-aging treatment in various biological model systems. The search for a mechanism of action resulted in identification of two independent targets. It has been found that VA non-enzymatically transfers electrons from NAD(P)H to oxidized glutathione. It has also been found that N2N1 participates in enzymatic transfer of electrons from NAD(P)H to corresponding substrates of NAD(P)H:quinone oxidoreductase (NQO1) or NADH:cytochrome b5 reductases.

The inventors believe that these compounds may improve the function of HSC and have therapeutic utility for the treatment of AA, MDS and other conditions associated with impaired HSC function. The acquired, so far, data clearly demonstrated that proposed therapy results in enrichment of stem cell population presented in adult tissues.

BRIEF DESCRIPTION OF THE FIGURES

The present invention may be more readily understood by reference to the following drawings, wherein:

FIGS. 1A-1I provide graphs and images showing a new high throughput method for simultaneous detection of senescence associated SAβG activity and ATP in culture of normal pre-aged cells identified two potent anti-aging scaffolds. (A). General schema of HTS. (B). Titration of most potent anti-aging compounds using proposed method with simultaneous detection of SAβG activity and ATP. (C). Structures and corresponding tautomeric forms of lead compounds. (D) Evaluation of possible genotoxic effect of experimental drugs in modified Ames test. 4-Nitroquinoline 1-oxide (4NQO) was used as a positive control. Both drugs did not show any detrimental effect on DNA integrity. (E) Identified anti-aging compounds increased the RLS of normal and progeroid cells in tissue culture. The general schema of RLS measurement in different cell types. (F) VA and N2N1 considerably extend RLS of normal human fibroblasts (NHDF) and stromal cells isolated from human normal bone marrow. (G). Gene expression analysis of fibroblasts treated with N2N1 or VA (RNAseq. exome) revealed the expression of some stem cell markers. (H) Fibroblasts derived from a patient diagnosed with Bloom syndrome also responded positively on treatment with N2N1 or VA, while fibroblasts derived from Werner syndrome patient did not respond. (I). Upper panel: Morphological appearance of NHDF at late passages with or without treatment. Lower panel: Cells were also fixed in paraformaldehyde and stained to detect SAβG. Treatment with the drugs substantially decreased the number of SAβG positive cells.

FIGS. 2A-2G provide graphs and images showing N2N1 and VA support HSC/progenitors populations under pressure of differentiation and tissue culture stress in vitro and in vivo. General schema of CFU (A) and LTC-IC assays (B). (C) Both VA and N2N1 compounds promote colonies formation in tissue culture derived from normal bone marrows. Representative result of three NBM is shown. (D) The morphology of cells at the end of 1st part of LTC-IC assay is shown. The total number of cells at this step of experiment was always larger in the samples treated with experimental drugs. (E) Treatment of mice with N2N1 promotes maintenance of normal HSC in vivo. Competitive repopulation assay performed on CD45.2 mice treated with N2N1. Summary of four animals, three hematopoietic tissues. (F) Both VA and N2N1 compounds promote colonies formation in tissue culture derived from aplastic anemia patients. Representative result of three patients is shown. (G) Treatment with VA of cancer cell lines was neither toxic nor pro-proliferative and does not support the growth of erythropoietin-dependent UT7 cells. N2N1 was partially toxic for the tested cancer cell lines. or AA bone marrows in CFU and LTC-IC assays.

FIGS. 3A-3C provide graphs and schemes showing the preliminary data that directed the plan to find the mechanism of action of identified anti-aging compounds. (A) Substantial decrease in oxidized sulfhydryl groups were detected after several days of treatment with VA. Both biotin-switch and Elman's reagent showed the increase in —SH group concentration after treatment with VA. (B) This result generated a list of possible enzymatic activities that potentially could be modulated by VA. The inventors decided to check if VA can participate in catalytic reactions performed by the enzymes involved in generation of reductive potential or its utilization by transferring the electrons to oxidized disulfide bonds t. (C) It has been demonstrated before that N2N1 can serve as a catalytic molecule in some redox reactions. In particular, catalytic reduction of molecular oxygen and cytochrome c was observed. Therefore, the inventors decided to take into account the most prominent enzymes that were noted to be involved into initiation or prevention aging-like traits.

FIGS. 4A 4B provide graphs and schemes showing VA's mechanism of action. The inventors found that VA can directly non-enzymatically transfer electrons from NAD (P)H to oxidized glutathione. (A) Different concentrations of VA were incubated with GssG in potassium phosphate buffer at pH 7.0, 37° C. While GsssG can alone oxidize NAD(P)H, addition of VA substantially increase the reaction rate. The effective concentrations of VA were similar to the detected for the extension of RLS in normal or progeroid cells. (B) The proposed molecular mechanism of glutathione reduction catalyzed by VA. The slightly acidic buffers (pH 7.0) supplemented with potassium (100 mM) were the preferable reaction conditions.

FIGS. 5A-5C provide graphs and schemes relating to the N2N1 mechanism of action. (A) The inventors found that N2N1 can enhance the rate of enzymatic NAD(P)H oxidation. No specific substrate was added into reaction mix, therefore, it was concluded that reaction was driven by slow reduction of molecular oxygen dissolved into reaction buffer. The hypothetical reaction equation is shown below reaction plots. (B) The proposed molecular mechanism of possible substrate reduction catalyzed by N2N1. (C) Addition of peroxide or cytochrome c into reaction allowed us to identify cytochrome c as the most preferable substrate for the N2N1 driven enzymatic reaction. Peroxide was reduced as well in non-enzymatic reaction, but at lower rate indicating that N2N1 is a potential anti-oxidant that drives the enzymatic reduction of molecular oxygen into peroxide and peroxide into water. It was interesting to notice that addition of cytochrome c to non-enzymatic reaction reduced the reaction rate. The result indicates that in the absence of enzyme(s) N2N1 tightly bonded to the presented in access cytochrome c molecules, most likely through complexing with the heme prosthetic group. The hypothetical reaction equation is show below the reaction plots.

DETAILED DESCRIPTION OF THE INVENTION

The present invention provides anti-aging compounds identified using the lead compounds violuric acid and 1-naphthoquinone-2-monoxime. The compounds are redox catalysts that appear to improve the function of hematopoietic stem cells. The compounds can be used to decrease the rate of aging in a subject, or to treat or decrease the risk of developing an age-related disease or disorder.

Definitions

The terminology as set forth herein is for description of the embodiments only and should not be construed as limiting of the invention as a whole. As used in the description of the invention and the appended claims, the singular forms "a", "an", and "the" are inclusive of their plural forms, unless contraindicated by the context surrounding such.

As used herein, the term "organic group" is used to mean a hydrocarbon group that is classified as an aliphatic group, cyclic group, or combination of aliphatic and cyclic groups (e.g., alkaryl and aralkyl groups). In the context of the present invention, suitable organic groups for the compounds of this invention are those that do not interfere with the anti-aging activity of the compounds. In the context of the present invention, the term "aliphatic group" means a saturated or unsaturated linear or branched hydrocarbon group. This term is used to encompass alkyl, alkenyl, and alkynyl groups, for example.

As used herein, the terms "alkyl", "alkenyl", and the prefix "alk-" are inclusive of straight chain groups and branched chain groups. Unless otherwise specified, these groups contain from 1 to 20 carbon atoms, with alkenyl groups containing from 2 to 20 carbon atoms. In some embodiments, these groups have a total of at most 10 carbon atoms, at most 8 carbon atoms, at most 6 carbon atoms, or at most 4 carbon atoms. Alkyl groups including 4 or fewer carbon atoms can also be referred to as lower alkyl groups. Alkyl groups can also be referred to by the number of carbon atoms that they include (i.e., $C_1$-$C_4$ alkyl groups are alky groups including 1-4 carbon atoms).

Cycloalkyl, as used herein, refers to an alkyl group (i.e., an alkyl, alkenyl, or alkynyl group) that forms a ring structure. Cyclic groups can be monocyclic or polycyclic and preferably have from 3 to 10 ring carbon atoms. A cycloalkyl group can be attached to the main structure via an alkyl group including 4 or less carbon atoms. Exemplary cyclic groups include cyclopropyl, cyclopropylmethyl, cyclopentyl, cyclohexyl, adamantyl, and substituted and unsubstituted bornyl, norbornyl, and norbornenyl.

Unless otherwise specified, "alkylene" and "alkenylene" are the divalent forms of the "alkyl" and "alkenyl" groups defined above. The terms, "alkylenyl" and "alkenylenyl" are used when "alkylene" and "alkenylene", respectively, are substituted. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-". Examples of suitable haloalkyl groups are chloromethyl, trifluoromethyl, and the like. Halo moieties include chlorine, bromine, fluorine, and iodine.

The term "aryl" as used herein includes carbocyclic aromatic rings or ring systems. Examples of aryl groups include phenyl, naphthyl, biphenyl, fluorenyl and indenyl. Aryl groups may be substituted or unsubstituted.

Unless otherwise indicated, the term "heteroatom" refers to the atoms O, S, or N. The term "heteroaryl" includes aromatic rings or ring systems that contain at least one ring heteroatom (e.g., O, S, N). In some embodiments, the term "heteroaryl" includes a ring or ring system that contains 2 to 12 carbon atoms, 1 to 3 rings, 1 to 4 heteroatoms, and O, S, and/or N as the heteroatoms. Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The terms "arylene" and "heteroarylene" are the divalent forms of the "aryl" and "heteroaryl" groups defined above. The terms "arylenyl" and "heteroarylenyl" are used when "arylene" and "heteroarylene", respectively, are substituted. For example, an alkylarylenyl group comprises an arylene moiety to which an alkyl group is attached.

When a group is present more than once in any formula or scheme described herein, each group (or substituent) is independently selected, whether explicitly stated or not. For example, for the formula —C(O)—NR$_2$ each R group is independently selected.

As a means of simplifying the discussion and the recitation of certain terminology used throughout this application, the terms "group" and "moiety" are used to differentiate between chemical species that allow for substitution or that may be substituted and those that do not so allow for substitution or may not be so substituted. Thus, when the term "group" is used to describe a chemical substituent, the described chemical material includes the unsubstituted group and that group with nonperoxidic O, N, S, Si, or F atoms, for example, in the chain as well as carbonyl groups or other conventional substituents. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, tert-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, cyanoalkyls, etc. On the other hand, the phrase "alkyl moiety" is limited to the inclusion of only pure open chain saturated hydrocarbon alkyl substituents, such as methyl, ethyl, propyl, tert-butyl, and the like.

The invention is inclusive of the compounds described herein in any of their pharmaceutically acceptable forms, including isomers (e.g., diastereomers and enantiomers), tautomers, salts, solvates, polymorphs, prodrugs, and the like. In particular, if a compound is optically active, the invention specifically includes each of the compound's enantiomers as well as racemic mixtures of the enantiomers. It should be understood that the term "compound" includes any or all of such forms, whether explicitly stated or not (although at times, "salts" are explicitly stated).

A subject, as defined herein, is an animal such as a vertebrate or invertebrate organism. In some embodiments, the subject is a single celled organism such as a yeast or bacteria. In other embodiments, the subject is a mammal such as a domesticated farm animal (e.g., cow, horse, pig) or pet (e.g., dog, cat). More preferably, the subject is a human. The subject may also be a subject at risk of developing an age-related disease. A subject can also be a subject for which an increased lifespan is desired.

The term "adult," as used herein, refers to subjects that are fully grown or developed, particularly with regard to sexual maturity. The term "adult" excludes infants or children, but includes elderly subjects. With regard to adult humans, an adult is typically a human having an age of 21 years or older, though the cutoff can vary from one individual to another. The term "adult" also encompasses nonhuman mammalian subjects at similar stages in their life cycle. For example, cats and dogs are typically considered adults at 1 year and older.

The term "elderly," as used herein, refers to older human subjects (e.g., middle age and above of 50 years and older, senior citizen and above of 65 years and older, or elderly and above of 80 years and older, etc.). The term "elderly" also encompass older nonhuman mammalian subjects at similar stages in their life cycles (e.g., 8-12 years and older for large dogs, 10-15 years and older for small and medium sized dogs, 15 to 20 years and older for cats, 15-18 months and older for mice, etc.).

Treat", "treating", and "treatment", etc., as used herein, refer to any action decreasing the rate of aging of a subject or providing a benefit to a subject having an age-related disease, including improvement in the condition through lessening or suppression of at least one symptom, delay in progression of the disease, etc.

As used herein, the term "prevention" includes either preventing or decreasing the risk of developing an age-related disease or disorder. This includes prophylactic treatment of those having an enhanced risk of developing an age-related disease or disorder. An elevated risk represents an above-average risk that a subject will develop an age-related disease or disorder, which can be determined, for example, through family history or the detection of genes causing a predisposition to developing an age-related disease or disorder. A subject can also have an increased risk of developing an age-related disease or disorder as a result of having an increased age and/or being elderly.

"Pharmaceutically acceptable" as used herein means that the compound or composition is suitable for administration to a subject for the methods described herein, without unduly deleterious side effects in light of the severity of the disease and necessity of the treatment.

The terms "therapeutically effective" and "pharmacologically effective" are intended to qualify the amount of each agent which will achieve the goal of decreasing disease severity while avoiding adverse side effects such as those typically associated with alternative therapies. The therapeutically effective amount may be administered in one or more doses. An effective amount, on the other hand, is an amount sufficient to provide a significant chemical effect, such as improving the maintenance of redox balance by a detectable amount.

Anti-Aging Compounds

In one aspect, the present invention provides anti-aging compounds. The anti-aging compounds include a variety of compounds identified by testing candidate compounds structurally similar to N2N1 or violuric acid. In one embodiment, the anti-aging compounds include compounds according to formula I, formula II, formula II, or formula IV:

I

II

III

IV wherein $R^1$-$R^6$ are selected from H, $CH_3$, $C_2H_5$, $C_3H_7$, $C_4H_9$, COOH, $C_2H_2$COOH, $OCH_3$, F, Cl, Br, I, $NH_2$, OH, SH, $SO_3$, $NO_2$, and $PO_3$ groups. The alkyl groups can be substituted or unsubstituted. In some embodiments, the compounds can be selected just from formula I, formula II, formula III, or formula IV. In some embodiments, the compound is 1-naphthoquinone-2-monoxime, which has the structure:

In another embodiment, the anti-aging compound is a compound according to formula V:

wherein $R^1$ or $R^2$ is selected from H, $CH_3$, $C_2H_5$, $C_3H_7$, $C_4H_9$, or phenyl groups, and X is selected from S, O, and NH. The alkyl or phenyl groups can be substituted or unsubstituted.

In some embodiments, X is O, while in other embodiments, X is S or NH. In some embodiments, the compound is violuric acid, which has the structure:

Methods of Decreasing the Rate of Aging or Treating or Preventing Age-Related Disease The inventors have identified small molecules that may act as artificial electron carrier/catalysts capable of acting as a sustainable redox mediator. Their anti-aging effects can be explained as a result of their ability to facilitate electron transfer between natural electron carriers and, in the long run, the normalization of mitochondrial dynamics and respiration in agent cells, which prolongs the availability of hematopoietic stem cells. As a result, the compounds with be useful for retarding the physiological and pathological consequences of replicative and chronological aging in different tissues and in particular connective, mesenchymal, and hematopoietic compartments. Because of the universal mechanism of action, the compounds of the invention are capable of decreasing the rate of aging in a wide variety of different types of subjects, including both vertebrate and invertebrate organisms.

One aspect of the invention provides methods of using the anti-aging compounds of formulas I, II, III, IV, and V, or any particular compound encompassed by these formulae, to decrease the rate of aging, or treat or prevent age-related disease. In one embodiment, the invention provides a method of decreasing the rate of aging of a subject, comprising administering a therapeutically effective amount of a compound of formula I, II, III, or IV to the subject. In a further embodiment, the invention provides a method of decreasing the rate of aging of a subject, comprising administering a therapeutically effective amount of a compound of formula V to the subject.

Aging represents the accumulation of physiological changes in a human being over time. Aging, as referred to herein, is distinct from development, and relates to primarily to the harmful physiological results that gradually occur as a result of aging and the passage of time after development is complete. Examples of the harmful effects of aging in humans include wrinkling of skin, cognitive decline, decreased hearing, decreased eyesight, decreased fertility, hair loss and/or graying, tissue oxidation, frailty, and cachexia. Because aging, as defined herein, occurs only after development is complete, in some embodiments, the method of decreasing the rate of aging is carried out in subjects who are adult subjects, while in other embodiments the method is carried out in elderly subjects.

In some embodiments, the decreased rate of aging primarily affects a particular aspect of aging. For example, in some embodiments, the decreased rate of aging represents a decreased rate in the development of any one of wrinkling of skin, cognitive decline, decreased hearing, decreased eyesight, decreased fertility, hair loss and/or graying, tissue oxidation, frailty, or cachexia. In some embodiments, the decreased rate of aging represents an improvement of the regenerative processes of connective tissues in aging, or a decrease in the age-related decline in the regenerative potential of mesenchymal and/or hematopoietic stem cells, or accelerated recovery of hematopoiesis after the injury of mesenchymal and/or hematopoietic stem cells.

Decreasing the rate of aging refers to slowing the accumulation of the harmful effects of aging over time. The decrease can be represented by a percentage change in the accumulation of the harmful effects of aging in subjects who are treated with the compounds of the invention, as compared to the accumulation of harmful effects of aging in normal, untreated subjects. The type of aging that is decreased is also referred to as "proximal aging," which are age-based effects that come about because of factors in the recent past, as compared with "distal aging," which is aging due to a cause in the subjects early life. Alternately, or in addition, the decrease can be represented by an increased lifespan of subjects treated with the anti-aging compounds. Accordingly, in some embodiments, the decrease in the rate of aging refers to about a 5% decrease, a 10% decrease, a 15% decrease, a 20% decrease, a 25% decrease, a 30% decrease, a 35% decrease, a 40% decrease, a 45% decrease, or a 50% decrease. Alternately, the decrease in the rate of aging leads to about a 5% increase in the lifespan of the subject, or about a 10%, 15%, 20%, 25%, 30%, 35%, 40%, 45%, or 50% increase in the lifespan of the subject. The qualifier "about" indicates that percentage change can vary by up to 2% in either direction; e.g., a 5% change includes a 3% change or a 7% change.

Aging is among the greatest known risk factors for most human diseases. Dillin et al., Curr Opin Cell Biol., 0: 107-112 (2014). Of the roughly 150,000 people who die each day across the globe, about two thirds—i.e., 100,000 per day—die from age-related causes. Accordingly, another aspect of the invention provides a method of treating or decreasing the risk of developing an age-related disease or disorder in a subject by administering a therapeutically effective amount of a compound of formula I, II, III, IV or V, or any particular compound encompassed by these formulae, to the subject. In one embodiment, the compound is a compound according to formula I, II, III, or IV, while in another embodiment, the compound is a compound according to formula V. In some embodiments, the subject is an adult subject, while in other embodiments the subject is an elderly subject.

A number of diseases and disorders are known to be age-related. An age-related disease is a disease where the risk of developing the disease is particularly associated with aging. In some embodiments, the age-related disease or disorder is selected from the group consisting of tumorigenesis and malignant cancer development, neurodegenerative disease, myocardial infarction, heart failure, atherosclerosis, hypertension, osteoarthritis, osteoporosis, sarcopenia, loss of bone marrow, cataract, multiple sclerosis, Sjogren's disease, rheumatoid arthritis, degraded immune function, diabetes, idiopathic pulmonary fibrosis, age-related macular degeneration, cerebral infarction, stroke, Alzheimer's disease, Parkinson's disease, Huntington's disease, and disorders caused by the decline in testosterone, estrogen, growth hormone, IGF-1, or energy production.

In some embodiments, the age-related disease or disorder is associated with mitochondrial function loss, telomere dysfunction, senescence deterioration and age-dependent cell loss, mitochondrial deterioration, and/or cell cycle-arrested state in post-mitotic cells. Mitochondrially-derived reactive oxygen species can mediate redox signaling or, in excess, cause cell injury and even cell death. Recent evidence suggests that mitochondrial ultrastructure is tightly coupled to reactive oxygen species generation, depending on the physiological status of the cell, and is involved in a wide variety of diseases. Jezek et al., Antioxidants (Basel), 7(1). pii: E13 (2018).

In some embodiments, the anti-aging compounds of the invention of formulas I, II, III, IV, and V are administered to a subject to treat a disease or condition associated with impaired stem cell function. For example, the anti-aging compounds can be administered to improve the survival and/or maintenance of hematopoietic stem cells in compromised tissues after irradiation or chemotherapy. The anti-aging compounds can also be used to improve the effectiveness of hematopoietic stem cell transplant in therapy of hematopoietic stem cell failure in cancers involving stem cell failure such as aplastic anemia or myelodysplastic syndrome.

Identification of Anti-Aging Compounds

An additional aspect of the invention includes methods for identifying compounds that may be used to decrease the rate of aging or treat or decrease the risk of developing an age-related disease in a subject. Potential agents suitable for testing are referred to herein as "candidate agents." A variety of different assays can be used to identify the ability of an agent to decrease the rate of aging or treat or decrease the risk of developing an age-related disease. For example, the ability of the compound to function as a redox catalyst can be evaluated. Procedures for carrying out these analyses are known to those skilled in the art, and many are described in Example 1 provided herein.

Candidate agents may also be tested in animal models. For example, the ability of anti-aging compounds to function as redox catalysts can be evaluated by testing their ability to stimulate hematopoiesis in bone marrow cells. The ability of the compounds to decrease the rate of aging can be evaluated in hematopoietic stem cells, or a tissue culture or animal model of HSC. Results are typically compared between control animals treated with candidate agents and the control cells or littermates that did not receive treatment.

Formulation and Administration of Anti-Aging Compounds

The present invention provides a method for administering one or more anti-aging compounds in a pharmaceutical composition. Examples of pharmaceutical compositions include those for oral, intravenous, intramuscular, subcutaneous, or intraperitoneal administration, or any other route known to those skilled in the art, and generally involves providing an anti-aging compound formulated together with a pharmaceutically acceptable carrier.

When preparing the compounds described herein for oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water may be used as a suitable carrier.

For intravenous, intramuscular, subcutaneous, or intraperitoneal administration, the compound may be combined with a sterile aqueous solution which is preferably isotonic with the blood of the recipient. Such formulations may be prepared by dissolving solid active ingredient in water containing physiologically compatible substances such as sodium chloride, glycine, and the like, and having a buffered pH compatible with physiological conditions to produce an aqueous solution, and rendering said solution sterile. The formulations may be present in unit or multi-dose containers such as sealed ampoules or vials.

Formulations suitable for parenteral administration conveniently comprise a sterile aqueous preparation of the active compound which is preferably made isotonic. Preparations for injections may also be formulated by suspending or emulsifying the compounds in non-aqueous solvent, such as vegetable oil, synthetic aliphatic acid glycerides, esters of higher aliphatic acids or propylene glycol.

The dosage form and amount can be readily established by reference to known treatment or prophylactic regiments. The amount of therapeutically active compound that is administered and the dosage regimen for treating a disease condition with the compounds and/or compositions of this invention depends on a variety of factors, including the age, weight, sex, and medical condition of the subject, the severity of the disease, the route and frequency of administration, and the particular compound employed, the location of the unwanted proliferating cells, as well as the pharmacokinetic properties of the individual treated, and thus may vary widely. The dosage will generally be lower if the compounds are administered locally rather than systemically, and for prevention rather than for treatment. Such treatments may be administered as often as necessary and for the period of time judged necessary by the treating physician. One of skill in the art will appreciate that the dosage regime or therapeutically effective amount of the inhibitor to be administered may need to be optimized for each individual. The pharmaceutical compositions may contain active ingredient in the range of about 0.1 to 2000 mg, preferably in the range of about 0.5 to 500 mg and most preferably between about 1 and 200 mg. A daily dose of about 0.01 to 100 mg/kg body weight, preferably between about 0.1 and about 50 mg/kg body weight, may be appropriate. The daily dose can be administered in one to four doses per day.

For example, the maximum tolerated dose (MTD) for anti-aging compounds can be determined in tumor-free athymic nude mice. Agents are prepared as suspensions in sterile water containing 0.5% methylcellulose (w/v) and 0.1% Tween 80 (v/v) and administered to mice (7 animals/group) by oral gavage at doses of 0, 25, 50, 100 and 200 mg/kg once daily for 14 days. Body weights, measured twice weekly, and direct daily observations of general health and behavior will serve as primary indicators of drug tolerance. MTD is defined as the highest dose that causes no more than 10% weight loss over the 14-day treatment period.

The anti-aging compounds can also be provided as pharmaceutically acceptable salts. The phrase "pharmaceutically acceptable salts" connotes salts commonly used to form alkali metal salts and to form addition salts of free acids or free bases. The nature of the salt is not critical, provided that it is pharmaceutically acceptable. Suitable pharmaceutically acceptable acid addition salts of the compounds may be prepared from an inorganic acid or from an organic acid. Examples of such inorganic acids are hydrochloric, hydrobromic, hydroiodic, nitric, carbonic, sulfuric, and phosphoric acid. Appropriate organic acids may be selected from aliphatic, cycloaliphatic, aromatic, araliphatic, heterocyclic, carboxylic, and sulfonic classes of organic acids, examples of which include formic, acetic, propionic, succinic, glycolic, gluconic, lactic, malic, tartaric, citric, ascorbic, glucoronic, maleic, fumaric, pyruvic, aspartic, glutamic, benzoic, anthranilic, mesylic, salicylic, p-hydroxybenzoic, phenylacetic, mandelic, ambonic, pamoic, methanesulfonic, ethanesulfonic, benzenesulfonic, pantothenic, 2-hydroxyethanesulfonic, toluenesulfonic, sulfanilic, cyclohexylaminosulfonic, stearic, algenic, γ-hydroxybutyric, galactaric, and galacturonic acids. Suitable pharmaceutically acceptable base addition salts of the compounds described herein include metallic salts made from aluminum, calcium, lithium, magnesium, potassium, sodium, and zinc. Alternatively, organic salts made from N,N'-dibenzylethylenediamine, chloroprocaine, choline, diethanolamine, ethylenediamine, meglumine (N-methylglucamine) and procaine may be used form base addition salts of the compounds described herein. All of these salts may be prepared by conventional means from the corresponding compounds described herein by reacting, for example, the appropriate acid or base with the compound.

Preparation of Anti-Aging Compounds

Compounds of the invention may be synthesized by synthetic routes that include processes analogous to those well known in the chemical arts, particularly in light of the description contained herein. The starting materials are generally available from commercial sources such as Aldrich Chemicals (Milwaukee, Wis., USA) or are readily prepared using methods well known to those skilled in the art (e.g., prepared by methods generally described in Louis F. Fieser and Mary Fieser, Reagents for Organic Synthesis, v. 1-19, Wiley, New York, (1967-1999 ed.) and similar texts known to those skilled in the art.

The present invention is illustrated by the following examples. It is to be understood that the particular examples, materials, amounts, and procedures are to be interpreted broadly in accordance with the scope and spirit of the invention as set forth herein.

EXAMPLES

Example I: Identification of Anti-Aging Compounds

Figures 1A, 1B, 1C, 1D, 1E, 1F, 1G, 1H, 1I:
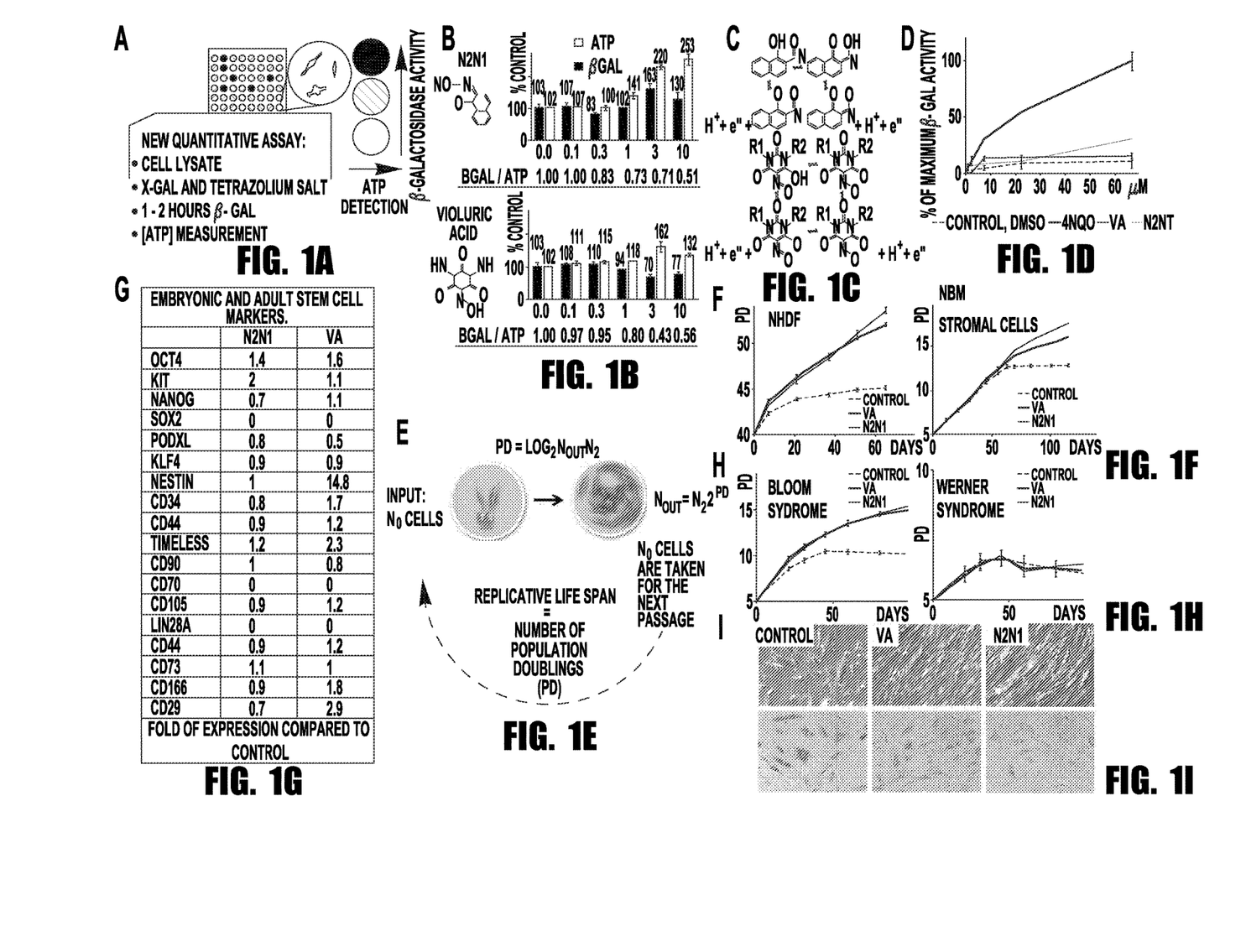

The inventors developed a new high-throughput screening (HTS) method for identification of anti-aging drugs (FIG. 1). The novel method was specifically designed for simultaneous detection of β-galactosidase activity in cell lysate followed by ATP detection by standard luciferase based assay. A common catalyst, nitro blue tetrazolium salt (NBT) was used in reaction to shorten the detection time from 24 hours to 1-2 hours and significantly increase signal to noise ratio. Altogether, the procedure allowed a simultaneous quantifiable detection of senescence associated β-galactosidase (SAβG) activity and evaluation of ATP level as a sign of improved proliferative capacity or cytotoxicity. Among tested cells were human mesenchymal cells or primary stromal cells from normal bone marrow (MSC), normal human dermal fibroblasts (NHDF) and bone marrow cells: total mononuclear fraction or CD34$^+$ enriched. Through screening of pre-senescence NHDF and MSC (FIGS. 1A and B) two lead compounds (VA and N2N1) were identified (FIG. 1C). Cells continued to replicate in the presence of these compounds and also had decreased expression of SAβG. The identified small molecules belongs to a redox catalysts that are able to delay aging associated phenotypes and eventually extend replicative lifespan (RLS) of freshly isolated human primary cells in tissue culture (FIG. 1F). The lead compounds have anti-aging properties and a chemical scaffold was described as combined electrophile-nucleophile redox catalyst (FIG. 1C). Violuric acid (2,4,5,6(1H,3H)-pyrimidine-tetrone 5-oxime)(Kim et al., Chem Phys Lett 371, 410-416 (2003)), is broadly used in biotechnology due to its high tolerance to temperature, pH variations, lack of toxicity, and biodegradability. Rahman et al., Sensors 10, 4855-4886 (2010). It is used as a very efficient electron transfer mediator (redox mediator) in reduction/oxidation processes supporting the global rate of electron transfer. N2N1 molecule, 1-naphthoquinone-2-monoxime, has been known before for the unique property to catalyze electron transfer from NAD(P)H preferably to cytochrome C and to some extent to molecular oxygen. The molecules of this structure are broadly used as redox catalysts in many biochemical and medical applications. Yoo, E. H. & Lee, S. Y., Sensors 10, 4558-4576 (2010).

In a large set of experiments, in a dose dependent manner these putative drugs substantially extended the RLS of primary fibroblasts, MSC (FIG. 1F), and most importantly progeroid fibroblasts (Bloom or Werner syndromes, FIG. 1H) with down-regulation of well-established senescence markers (CDKN2a, p21, and SAβG (FIG. 1I). Normal telomere length was retained after treatment with both compounds at late passages of fibroblasts tissue culture. RNA-seq data revealed that treatment of NHDF results in up-regulation of classic markers of stemness: c-Kit, Oct-3/4, Nestin and CD34 (FIG. 3F).

While these compounds may have many applications, the inventors have focused on potential usage of these agents to improve the function of HSC in BMF. They have first applied them in a battery of tissue culture assays measuring i) exhaustion kinetics of HSC and ii) hematologic toxicity. The LD$_{50}$ in hematopoietic colony assays was 5 mM and 15 μM for VA and N2N1 respectively. The inventors then focused our studies on HSC performance measured in CFU assay and in LTC-IC (FIG. 2), the best in vitro surrogate assay for the quantification and functional assessment of HSCs. The potential positive impact of identified pro-survival catalysts on viability and propagation of HSC was evaluated in methylcellulose cultures, classic CFU assay, long-term culture colony-initiating (LTC-IC) cell assays (FIGS. 2A, B and C) and competitive repopulation assay based on CD45.1/2 mouse model (FIG. 2E).

Figures 2A, 2C:
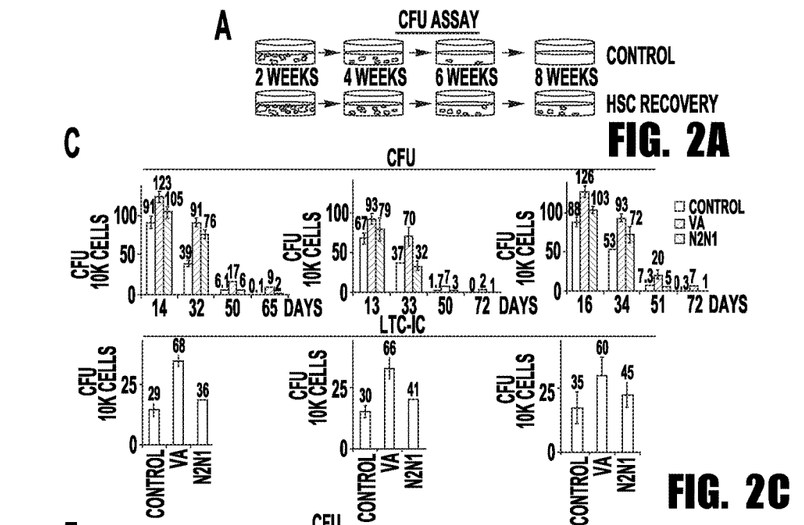
Figure 2B:
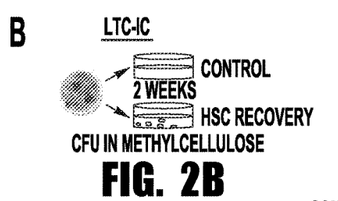
Figure 2D:
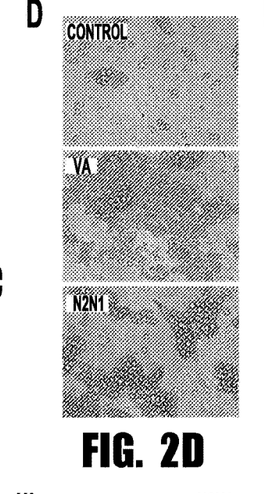
Figure 2E:
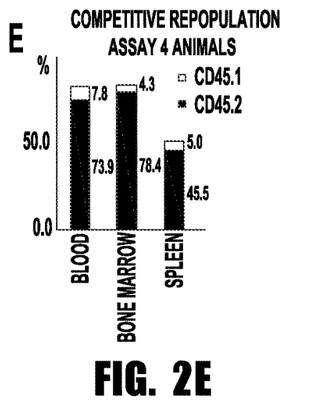
Figure 2F:
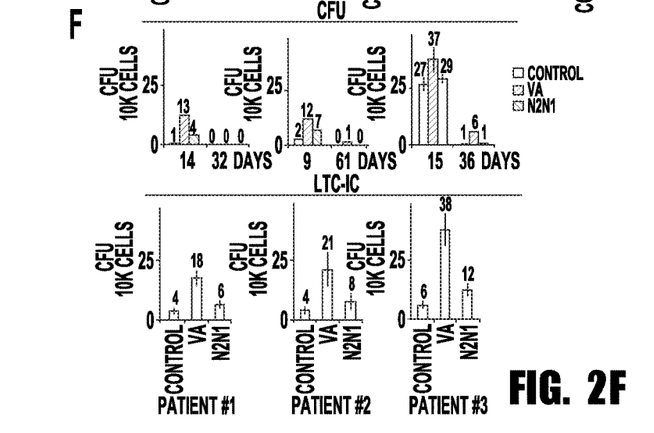
Figure 2G:
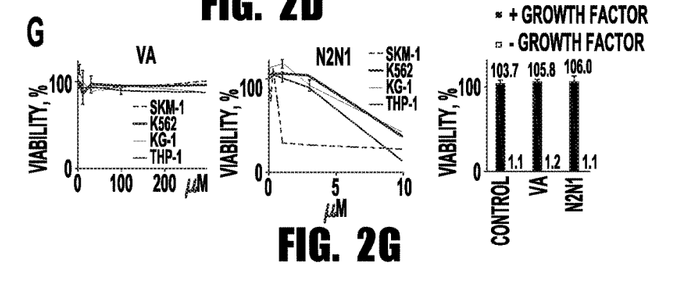

As a starting point for clinical application of identified redox catalysts, the inventors tested them on their ability to stimulate hematopoiesis in normal and damaged bone marrow cells, isolated from the patients with severe AA (FIGS. 2C and F). Very promising data was obtained, confirming the original idea that these small molecules can support propagation of both normal HSC and stem cells presented in damaged or disease bone marrow. Conversely, no pro-survival effects were observed in cultures of leukemic cell lines (FIG. 2G).

The potential positive impact of identified pro-survival catalysts on viability and propagation of HSC was evaluated in competitive repopulation assay based on CD45.1/2 mouse model, a "gold standard" for HSC performance. The pilot experiment with CD45.2 mice treated with N2N1 for one month (in drinking water, ~2.0 mg/kg) demonstrated that the treatment resulted in both increased number of HSC or/and increased repopulation capacity than placed in an identical environment together with non-treated HSCs (FIG. 2E).

Figure 3A:
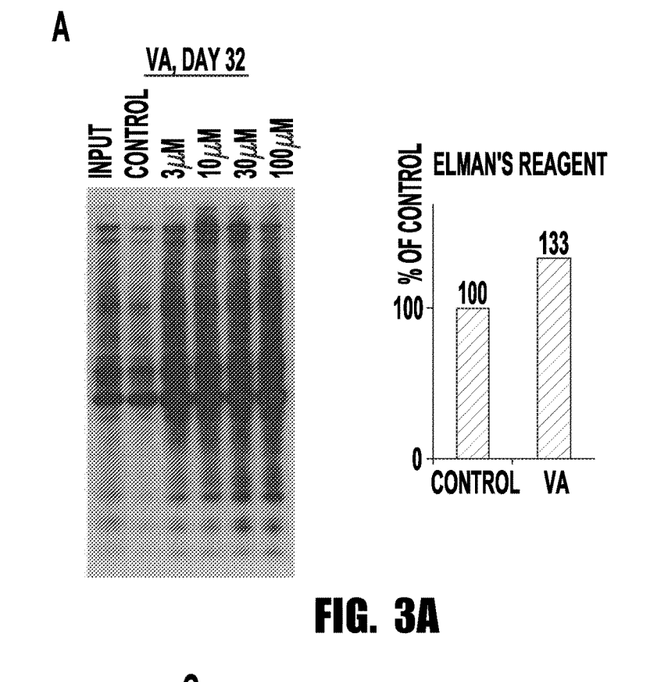
Figure 3B:
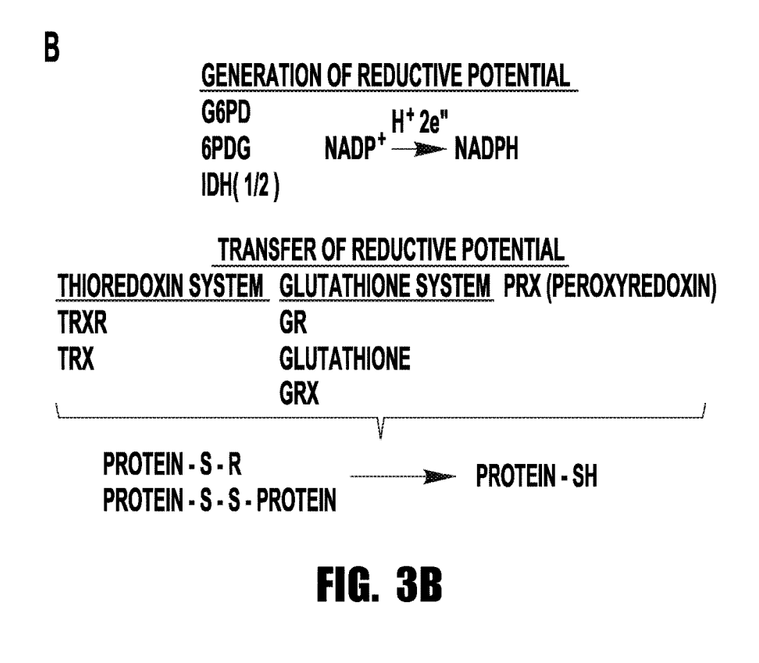

Based on results obtained on tissue cultured cells (increased RLS) and an increase in the numbers of HSC surrogate cells (LTC-IC or CFU), the inventors set their future goal to develop a novel pharmacological treatment for AA patients and potentially for other BMF. They have examined the most prominent features of cellular aging: telomere shortening, mitochondrial dysfunction or decline in respiratory capacity and shift in intracellular redox balance toward more oxidized environment. The maintenance of telomere length was observed in cells treated with VA or N2N1 normal fibroblasts. Yet, control, untreated mesenchymal cells went into senescence crisis without telomere shortening and treatment did not change their telomere length. While identified compounds can be described as redox mediators, the inventors could not detect any immediate (within few minutes or even hours) responses in mitochondrial respiration rate or changes in the efficacy of glycolysis after addition of the compounds into tissue culture medium (tested on Seahorse apparatus). The only persistent effect of VA was considerable reduction in global protein disulfide bonds (up to 30%) detected by Elman's reagent or direct labelling of reduced sulfhydryl groups with biotin-switch assay (FIG. 3A). That brought the reductive hypothesis to the inventors' attention. The redox potential is controlled by sophisticated set of diverse enzymes and this system is fed from generation of NADPH by multiple hydrogenases (FIG. 3B). Among them, the glucose-6-phosphate dehydrogenase (G6P) is most important, because it controls the rate limiting step of pentose phosphate pathway. The other important dehydrogenases are isocytrate dehydrogenases (cytoplasmic and mitochondrial, IDH1/2) and 6-phosphogluconate dehydrogenase (6PG). The next antioxidant cellular protection layer is thioredoxin and glutathione systems (FIG. 3B). The first one is composed of thioredoxin reductase (TrxR) and thioredoxin. Thioredoxin reduces disulfide bonds, while TrxR reduces oxidized thioredoxins at the expense of NADPH. Glutathione can reduce oxidized or modified proteins by itself or can be used in combination with glutaredoxin to protect sulfhydryl groups from oxidation. It can also be used by other, functionally and structurally similar proteins like peroxiredoxin and a big set of other redoxins to modify —SH or it can be targeted against harmful hyper reactive molecules like peroxides and free radicals. The oxidized glutathione is also reduced by glutathione reductase (GR) at the expense of NADPH oxidation.

Figure 4A:
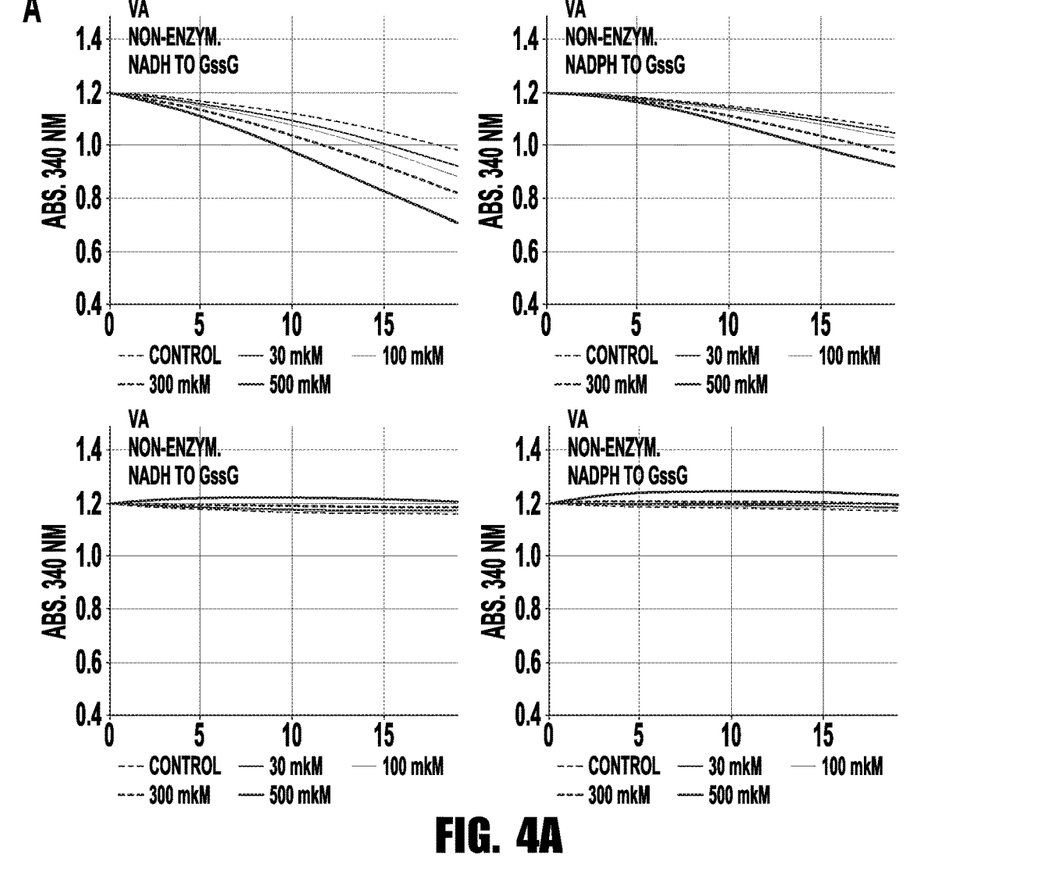
Figure 4B:
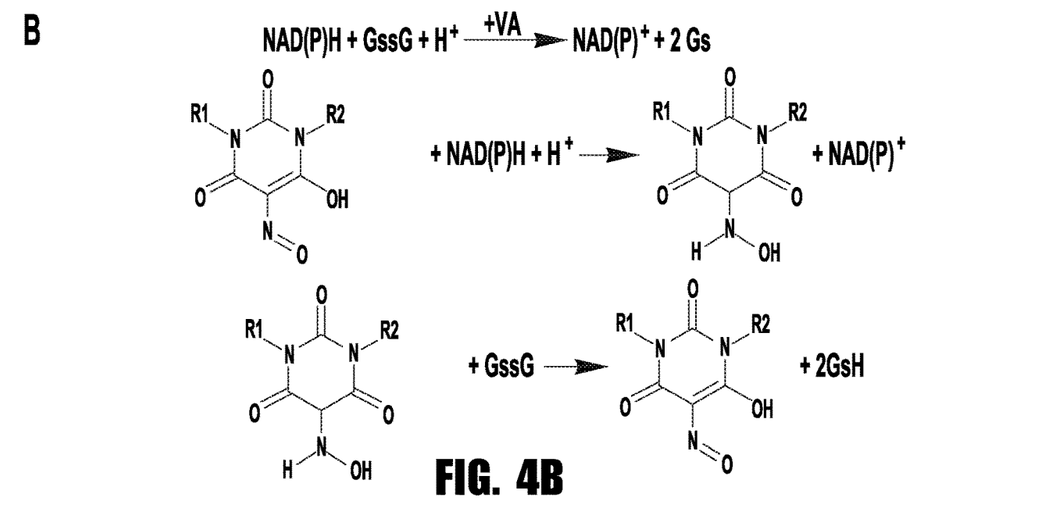

Lead compounds were tested on their possible catalytic amelioration of enzyme kinetics with all above mentioned proteins: recombinant and presented in cellular lysates. As a result, it was found that VA can non-enzymatically transfer electrons from NAD(P)H to oxidized glutathione (FIGS. 4A and B).

Figure 3C:
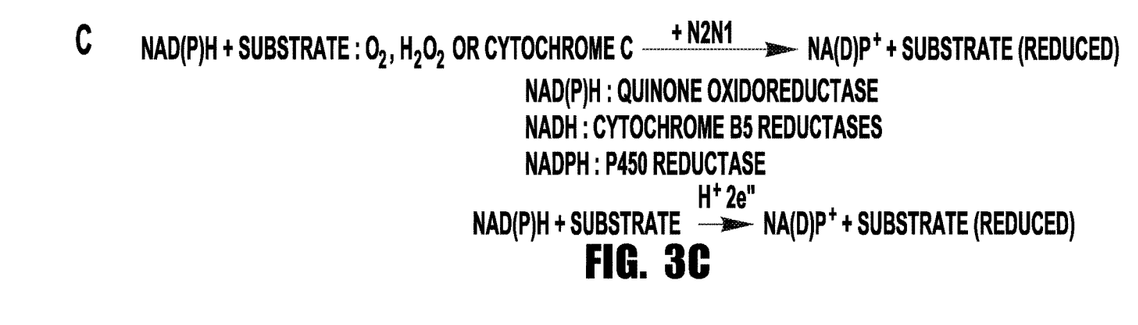
Figures 5A, 5B, 5C:
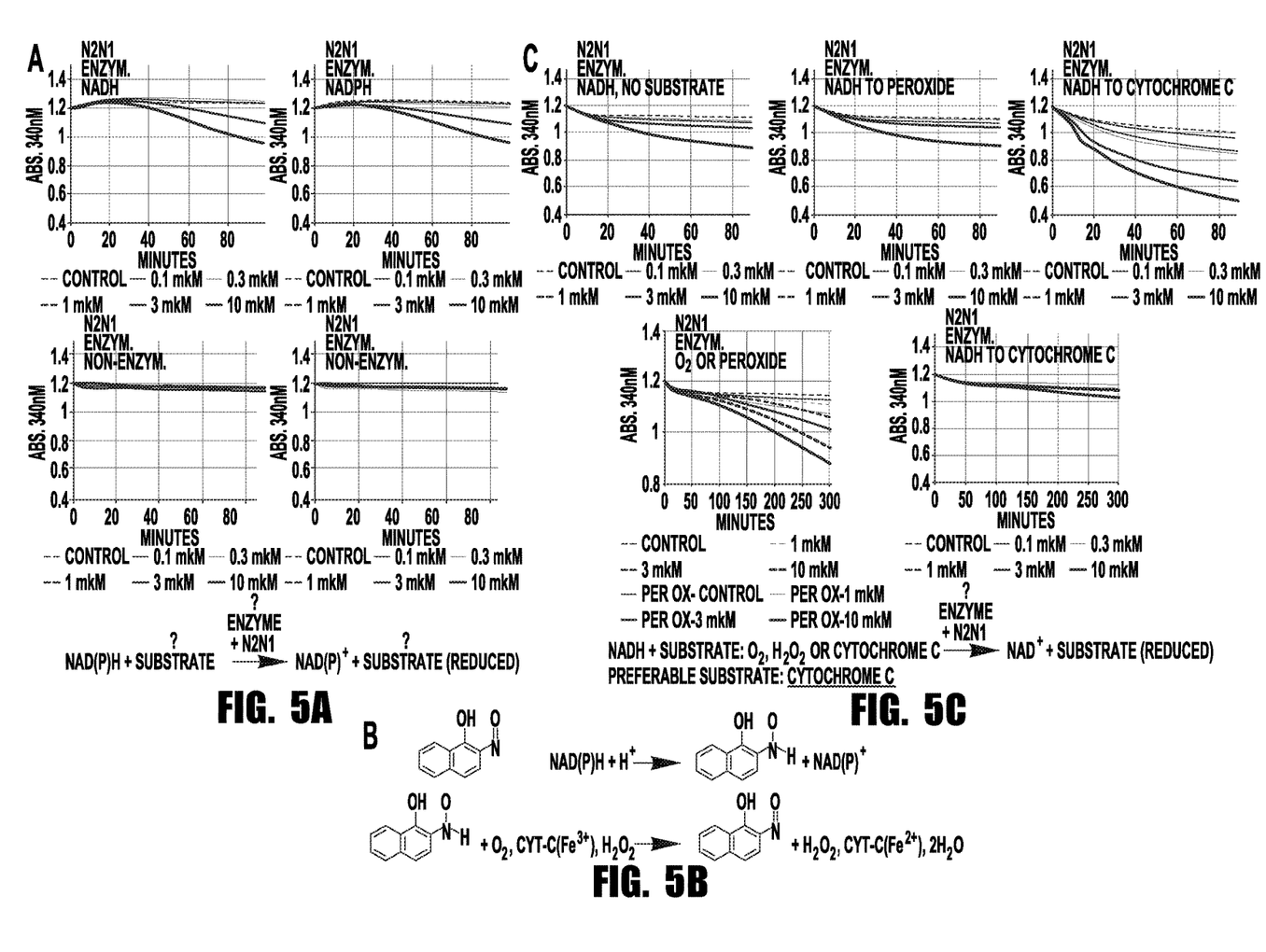

The inventors and others (Leskovac, V., Svircevic, J., Trivic, S., Popovic, M. & Radulovic, M. Reduction of aryl-nitroso compounds by pyridine and flavin coenzymes. The International journal of biochemistry 21, 825-834 (1989)) also found that N2N1 participates in enzymatic reduction of NAD(P)H (FIG. 5A). Small amount of N2N1 (1 µM) actively catalyze the enzymatic reduction of NADH and NADPH, thus generating a $NAD^+$ reach intracellular environment which is very favorable for stem cell self-renewal (Fang et al., Cell metabolism, 24, 566-581 (2016)) and promotes longevity (Fang et al., Trends in molecular medicine 23, 899-916 (2017)), both in tissue culture and organisms. Bonkowski et al., Nature reviews. Molecular cell biology 17, 679-690 (2016); Orr et al., Antioxidants & redox signaling 19, 788-803 (2013). It quite possible, that NAD (P)H oxidation catalyzed by N2N1 is performed by NADH: cytochrome b5 reductases (CYB5 . . . ) or NAD(P)H: quinone oxidoreductase (NQO1) reductase (FIG. 3C). The inventors found by RNA-seq analysis that fourteen genes from CYB5 family were expressed in normal fibroblast. NQO1 was also detected at the high level of expression. These reductases connect aerobic metabolism with aging by directed electron flow from NAD(P)H to oxygen, cytochrome C, and peroxide. Jimenez-Hidalgo et al., Aging cell 8, 140-151 (2009).

With all these proteins in mind and to further elaborate on mechanism behind N2N1 anti-aging effect and to find a protein target for this drug, different electron acceptors were tested in non-enzymatic and enzymatic setups. The inventors found that cytochrome c was the most potent electron acceptor in the reactions catalyzed by N2N1 and electrons can be transferred from both NADH and NADPH (FIG. 5C). If used in non-enzymatic reaction, N2N1 preferentially reduced peroxide over molecular oxygen dissolved in reaction buffer. While enzymatic reduction of cytochrome c runs substantially faster, the possible involvement of N2N1 in peroxide elimination can have an important consequence. It has been comprehensively demonstrated that peroxide produced by mitochondria or by some cytoplasmic enzyme could be a very prominent signaling molecule that controls multiple pathways including apoptosis and aging. Giorgio et al., Nat Rev Mol Cell Biol., 8, 722-728 (2007).

Figure 6A:
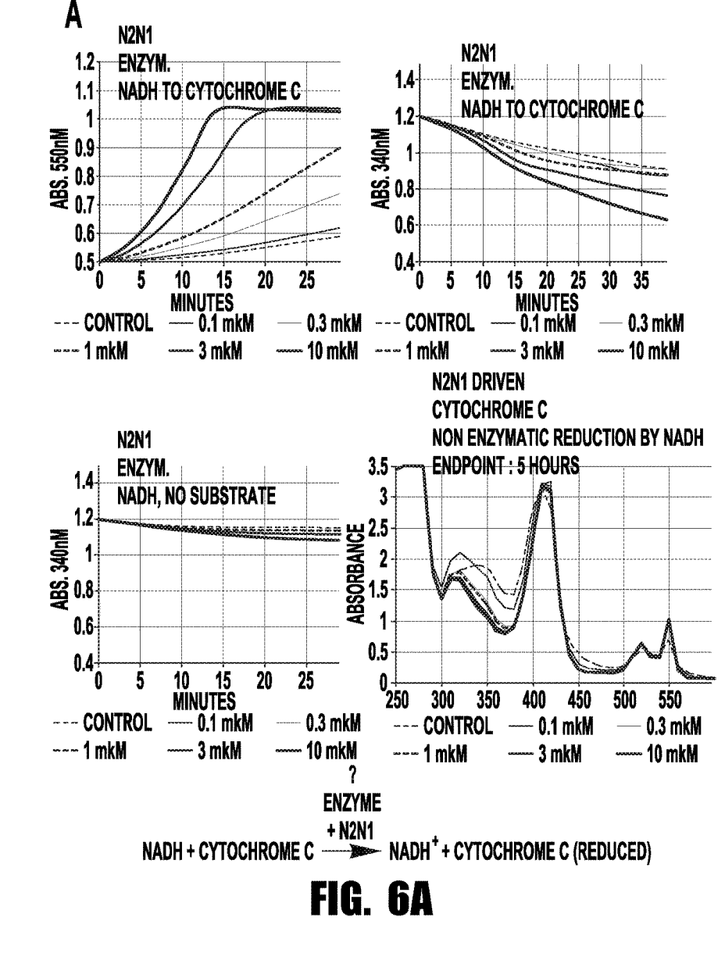
FIGS. 6A-6B provide graphs showing the enzymatic reduction of cytochrome C catalyzed by N2N1 can utilize both NADH and NADPH. (A) The enzymatic electrons transfer from NADH to cytochrome c driven by N2N1 was monitored by decrease in absorption at 340 nm (NADH) and increase in absorption at 550 nm (cytochrome c). The absorbance spectrum was screened at the end of the reaction (~1 hour). The hypothetical reaction equation is shown below the reaction plots. (B) The enzymatic electrons transfer from NADPH to cytochrome c driven by N2N1 was monitored by decrease in absorption at 340 nm (NADPH) and increase in absorption at 550 nm (cytochrome c). The hypothetical reaction equation is shown below the reaction plots.
Figure 6B:
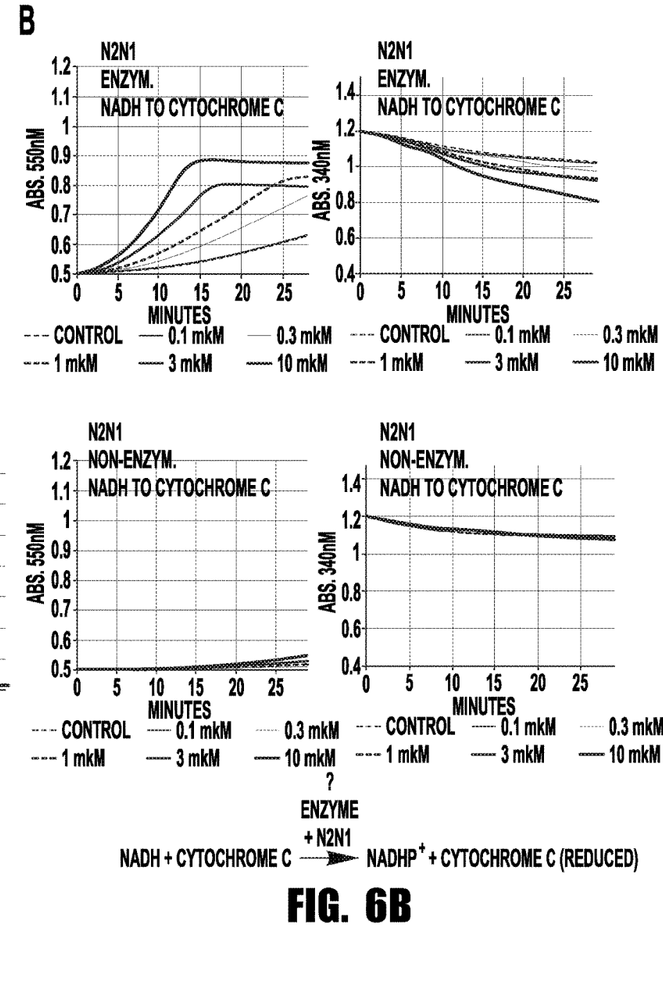

On the next step, the enzymatic oxidation of NADH or NADPH was examined in parallel in the presence of cytochrome c performed in the presence of different amount of N2N1 in reaction buffer (FIG. 6). The inventors observed dose dependent reduction of cytochrome c with relatively high reaction rate: the reduction of 0.5 mM cytochrome c can be completed within 10-15 minutes. The most important conclusion from these experiments is that the enzymes catalyzing reduction of cytochrome c can use both NADH and NADPH. That narrows down the list of possible proteins to three NAD(P)H dependent oxidoreductases: NADH:ubiquinone oxidoreductase (Complex I); NADH:P450 reductase (POR); NADH:cytochrome b5 reductase; and NAD(P)H:quinone oxidoreductase (NQO1).

Figure 7A:
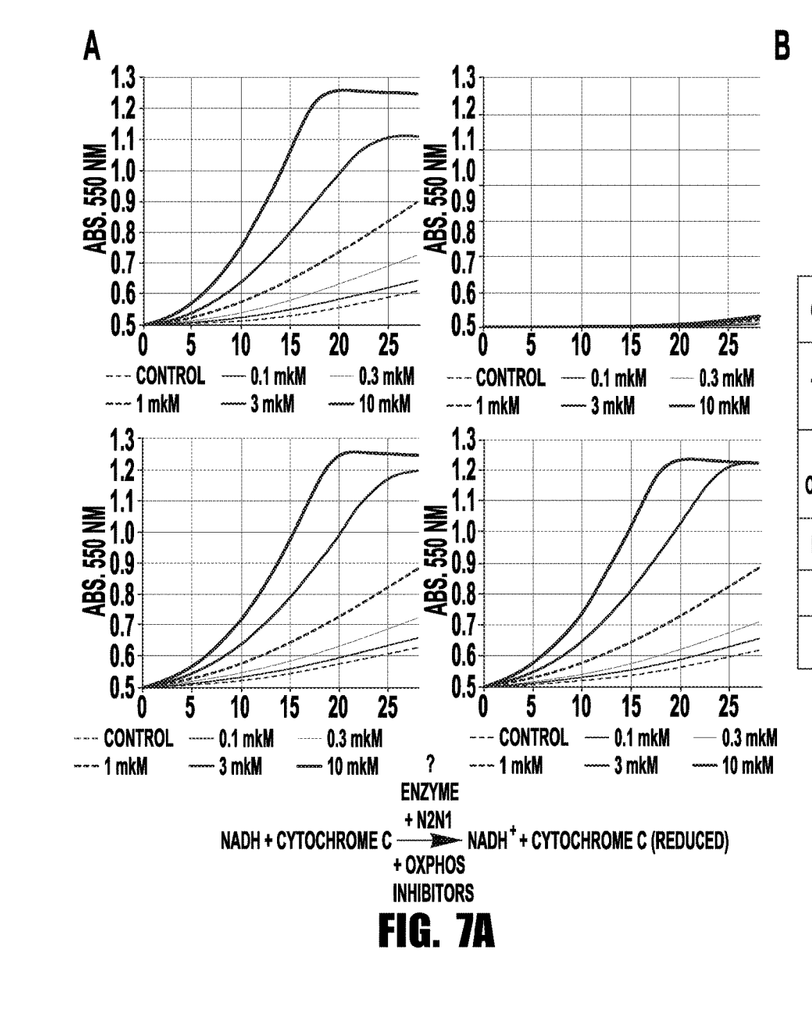
FIGS. 7A-7B provide graphs showing (A) The inhibitors of oxidative phosphorylation rotenone and antimycin A did not suppress the enzymatic reduction of cytochrome c catalyzed by N2N1. To evaluate possible participation of mitochondrial NADH oxidoreductases, in particular Complex I and III, the reduction of NADH was run in the presence of rotenone or antimycin A (2 µM). The acquired data allowed us to specify the most probable candidate that carry out the transfer electrons from NAD(P)H to cytochrome C driven by N2N1. The NQO1 protein would be the most likely candidate, while proteins from CYB5 family still cannot be ruled out.
Figure 7B:
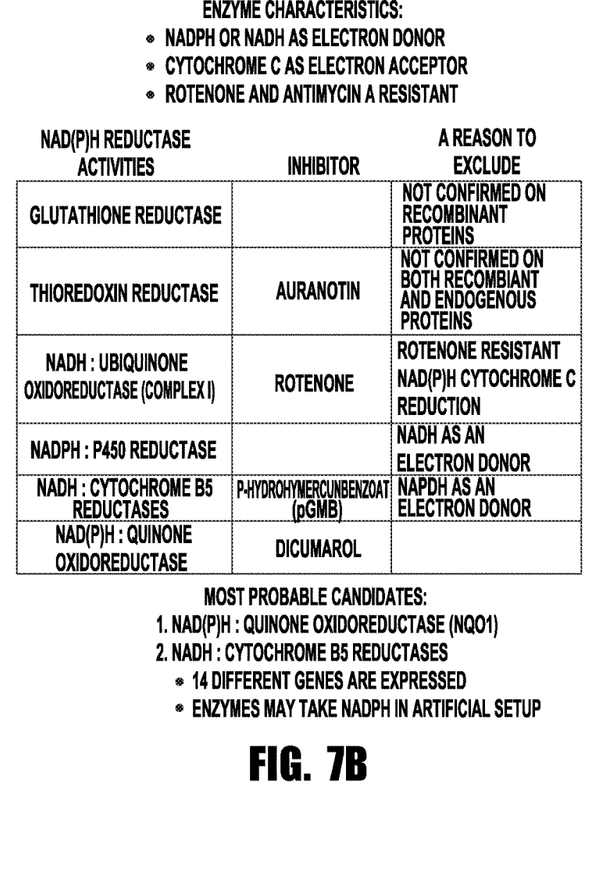

An experiment with the inhibitors of oxidative phosphorylation ruled out the Complex I as a target of N2N1 (FIG. 7A). The inventors have already demonstrated that both reductive molecules NADH and NADPH can effectively participate in N2N1 catalyzed reduction of cytochrome c. Therefore, the most probable candidate is NQO1 protein which can utilize both NADH and NADPH for the reduction of CoQ. On the other hand, CYB5 proteins are ubiquitously expressed in NHDF and it is still possible that they can use NADH as an electron acceptor in experimental set up as well (FIG. 7B).

Based on preliminary data that unequivocally demonstrated the possibility of pharmacological boost of HSC compartment both in tissue culture and animals, the inventors envision the development of innovative method for significantly improved efficiency of HSC isolation and potentially other adult stem cell in vitro. The further development of these drugs along with deeper understanding of their protein targets would make a great impact on understanding of HSC biology and treatment of corresponding disease with functional HSC deficit. Further research is being made with application of protein specific inhibitors to single out the target protein of N2N1 redox mediator.

Figure 8A:
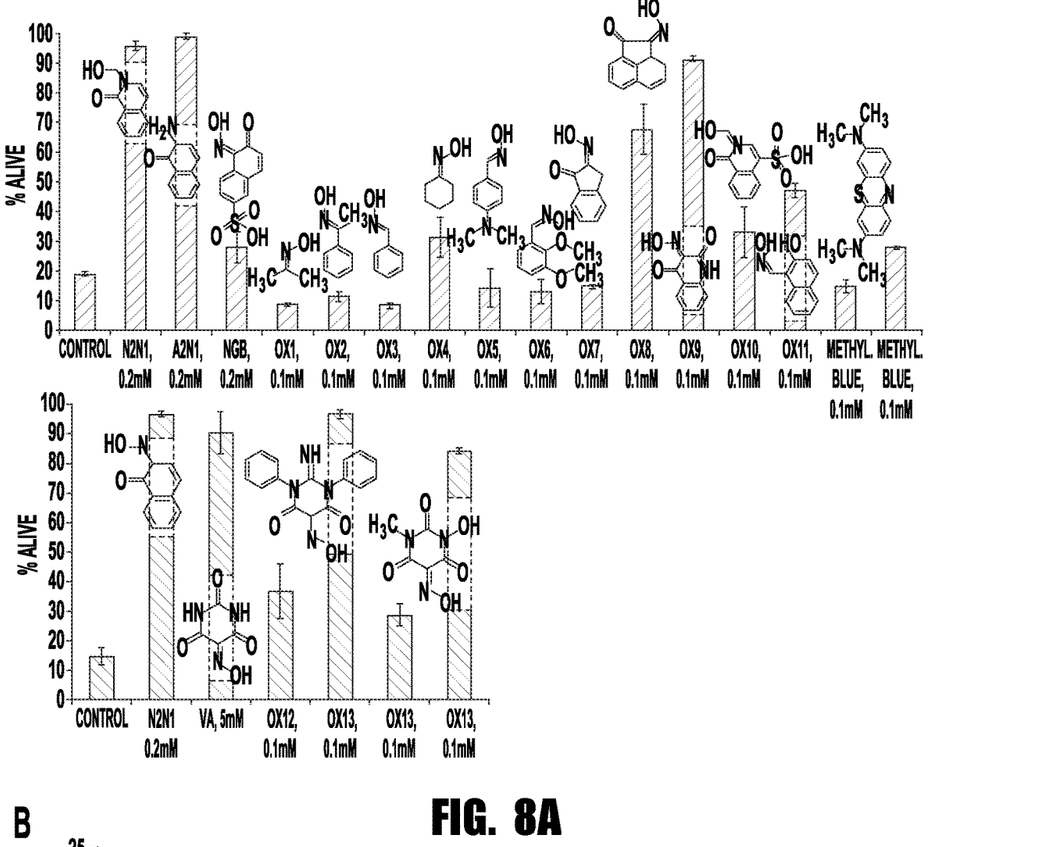
FIGS. 8A-8B provide graphs showing the effect of various small molecules on the ability of C. elegans to survive (A) under conditions of prolonged anoxia/hypoxia and (B) under hypoxic/anoxic atmosphere without added nitrite.
Figure 8B:
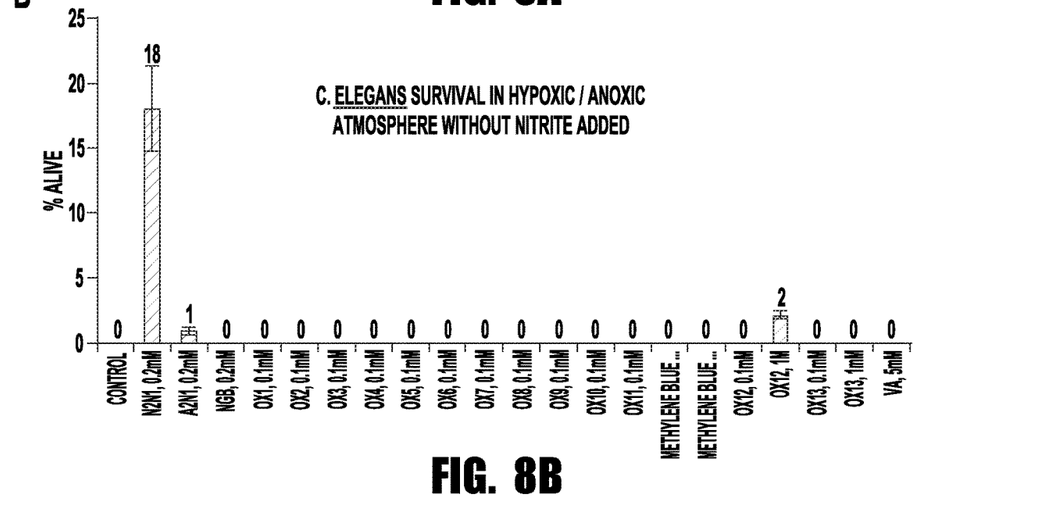

Example II: Multidrug Screen for Agents that could Decrease Senescence and Overcome Proliferative Block A set of functionally and structurally related small molecules was discovered having the ability to substantially extend the replicative lifespan of normal human cells (fibroblasts, stromal cells, hemaotopoietic stem cells), the chronological lifespan of C. elegans, and the replicative lifespan of wild type S. cerevisiae. The ability of the compounds to protect C. elegans from prolonged anoxia/hypoxia is shown in FIG. 8A, while the affect of the compounds on C. elegans survival in hypoxic/anoxic atmosphere without nitrite added is shown in FIG. 8B.

The complete disclosure of all patents, patent applications, and publications, and electronically available materials cited herein are incorporated by reference. The foregoing detailed description and examples have been given for clarity of understanding only. No unnecessary limitations are to be understood therefrom. In particular, while various theories are presented describing possible mechanisms through with the compounds are effective, the compounds are effective regardless of the particular mechanism employed and the inventors are therefore not bound by theories described herein. The invention is not limited to the exact details shown and described, for variations obvious to one skilled in the art will be included within the invention defined by the claims.

What is claimed is:

1. A composition comprising an anti-aging compound according to formula V:

wherein $R^1$ and $R^2$ are selected from H, $CH_3$, $C_2H_5$, $C_3H_7$, $C_4H_9$, and phenyl groups, and X is NH.

2. The composition of claim 1, further comprising a pharmaceutically acceptable carrier.

* * * * *